(12) United States Patent
Bray

(10) Patent No.: US 8,556,183 B2
(45) Date of Patent: Oct. 15, 2013

(54) SYSTEMS AND METHODS INVOLVING TRANSFERABLE IDENTIFICATION TAGS

(76) Inventor: Gregory D. Bray, Fortville, IN (US)

( * ) Notice: Subject to any disclaimer, the term of this patent is extended or adjusted under 35 U.S.C. 154(b) by 0 days.

(21) Appl. No.: 13/178,583

(22) Filed: Jul. 8, 2011

(65) Prior Publication Data

US 2013/0008960 A1  Jan. 10, 2013

(51) Int. Cl.
| | |
|---|---|
| *G06K 19/00* | (2006.01) |
| *G06K 19/06* | (2006.01) |
| *G06K 7/10* | (2006.01) |
| *G06K 7/14* | (2006.01) |
| *A61M 5/00* | (2006.01) |
| *A61M 5/32* | (2006.01) |
| *A61M 5/31* | (2006.01) |

(52) U.S. Cl.
USPC ...... 235/487; 235/454; 235/462.01; 235/492; 604/189; 604/192; 604/240; 604/243

(58) Field of Classification Search
USPC ............... 235/462.01, 487, 492, 454, 385; 304/189, 192, 197, 198, 240, 243
See application file for complete search history.

(56) References Cited

U.S. PATENT DOCUMENTS

| | | | |
|---|---|---|---|
| 2,072,853 A | | 3/1937 | Baxter |
| 4,457,437 A | * | 7/1984 | Heath, Jr. ........................ 215/224 |
| 4,548,601 A | * | 10/1985 | Lary .............................. 604/204 |
| 4,650,475 A | * | 3/1987 | Smith et al. ................... 604/189 |
| 4,921,277 A | | 5/1990 | McDonough |
| 4,993,571 A | | 2/1991 | Conti |
| 5,145,646 A | * | 9/1992 | Tyranski ........................ 422/547 |
| 5,284,263 A | * | 2/1994 | Papciak ......................... 215/230 |
| 5,344,780 A | * | 9/1994 | Nonboe ........................... 436/21 |
| 5,417,326 A | | 5/1995 | Winer |
| 5,692,640 A | * | 12/1997 | Caulfield et al. ................. 221/70 |
| 5,716,346 A | * | 2/1998 | Farris ............................. 604/243 |
| 5,829,589 A | * | 11/1998 | Nguyen et al. ................ 206/366 |
| 5,895,377 A | | 4/1999 | Smith et al. |
| 5,971,972 A | * | 10/1999 | Rosenbaum ................... 604/411 |
| 6,045,538 A | * | 4/2000 | Farris ............................. 604/243 |
| 6,059,132 A | * | 5/2000 | Benjamin ...................... 215/206 |
| 6,585,134 B2 | * | 7/2003 | Farris .............................. 222/95 |
| 6,764,463 B1 | * | 7/2004 | Farris .............................. 604/82 |
| 6,918,418 B1 | * | 7/2005 | Farris ............................. 141/319 |
| 7,115,113 B2 | | 10/2006 | Evans et al. |
| 7,161,488 B2 | | 1/2007 | Frasch |
| 7,559,483 B2 | | 7/2009 | Hickle et al. |
| 7,810,726 B2 | | 10/2010 | de la Huerga |

(Continued)

FOREIGN PATENT DOCUMENTS

WO   2011116462 A1   9/2011

*Primary Examiner* — Daniel Walsh
(74) *Attorney, Agent, or Firm* — Krieg DeVault LLP

(57) ABSTRACT

Systems and methods involving transferrable identification tags are provided. In one embodiment, a system includes a delivery device, a container, and a tag coupled to the container and configured to store information related to contents of the container. The delivery device is engageable with the tag and at least a portion of the contents of the container are transferrable from the container to the delivery device following its engagement with the tag. The tag is removable from the container in engagement with the delivery device such that the delivery device carries the tag following its removal. In one form, a frangible member is coupled to and extends between the tag and the container, and the tag is removable from the container by the delivery device upon breakage of the frangible member. Other embodiments include unique methods, systems, kits, assemblies, equipment, and/or apparatus which involve transferrable identification tags.

32 Claims, 9 Drawing Sheets

(56) References Cited

U.S. PATENT DOCUMENTS

| | | | |
|---|---|---|---|
| 2001/0010936 A1* | 8/2001 | Richards et al. | 436/49 |
| 2001/0022279 A1* | 9/2001 | Denyer et al. | 206/438 |
| 2002/0035820 A1* | 3/2002 | Farris | 53/467 |
| 2003/0164401 A1 | 9/2003 | Andreasson et al. | |
| 2004/0046020 A1 | 3/2004 | Andreasson et al. | |
| 2004/0097882 A1* | 5/2004 | DiBiasi et al. | 604/199 |
| 2004/0186437 A1* | 9/2004 | Frenette et al. | 604/189 |
| 2005/0171484 A1* | 8/2005 | Jangula | 604/198 |
| 2006/0285913 A1* | 12/2006 | Koptis | 401/205 |
| 2007/0078428 A1* | 4/2007 | Reynolds et al. | 604/411 |
| 2007/0187475 A1* | 8/2007 | MacLeod | 235/375 |
| 2007/0225672 A1 | 9/2007 | Wagner | |
| 2007/0296599 A1* | 12/2007 | Wang et al. | 340/572.8 |
| 2008/0035659 A1 | 2/2008 | Ricker et al. | |
| 2008/0106388 A1* | 5/2008 | Knight | 340/10.42 |
| 2008/0191013 A1 | 8/2008 | Liberatore | |
| 2008/0255515 A1* | 10/2008 | Grinberg | 604/111 |
| 2008/0255523 A1* | 10/2008 | Grinberg | 604/192 |
| 2009/0306620 A1* | 12/2009 | Thilly et al. | 604/415 |
| 2010/0000960 A1* | 1/2010 | Anderson | 215/228 |
| 2010/0036678 A1 | 2/2010 | Bray | |
| 2010/0112815 A1* | 5/2010 | O'Dougherty et al. | 438/689 |
| 2010/0204669 A1* | 8/2010 | Knight | 604/403 |
| 2010/2045056 | 9/2010 | Braun et al. | |
| 2011/0004165 A1* | 1/2011 | Iio et al. | 604/197 |
| 2011/0264069 A1* | 10/2011 | Bochenko | 604/404 |
| 2012/0037266 A1* | 2/2012 | Bochenko | 141/1 |
| 2012/0095415 A1* | 4/2012 | Sharvit et al. | 604/244 |
| 2013/0012908 A1* | 1/2013 | Yeung | 604/404 |

* cited by examiner

SYSTEMS AND METHODS INVOLVING TRANSFERABLE IDENTIFICATION TAGS

The present application relates to systems and methods involving transferable identification tags and more particularly, but not exclusively, to identification tags that are transferable from a container to a delivery device following removal of at least a portion of the contents from the container with the delivery device.

Many products and materials are provided or stored in a container from which they must be removed for further use. In certain forms, the products and materials are transferred from the container to an intermediate device which may be used for application, administration, storage, or other handling of the materials and products. In some instances, the intermediate devices can be set aside for a period of time and/or transferred or exchanged between a number of handlers. In addition, the products and materials may have an undistinguishable appearance, and the intermediate devices may also fail to include any information identifying the materials and products which are contained therein. In certain situations, the foregoing and other factors can result in misuse or misapplication of the materials and products following their removal from the container.

For example, by way of non-limiting example, many pharmaceutical products are provided or stored in a container or vial and must be removed from the container with a delivery device, such as a syringe, for administration to a patient. Many pharmaceuticals have an undistinguishable appearance and/or share similar physical and visual characteristics with other pharmaceuticals, often leading to difficulties for healthcare workers in visually identifying a specific pharmaceutical or differentiating between multiple pharmaceuticals and/or varying concentrations of a single pharmaceutical. For example, two separate pharmaceuticals each used to treat a distinct medical condition may have identical, clear appearances, or different concentrations of a single pharmaceutical may have identical, clear appearances.

While labels can be affixed to the containers to identify details of the pharmaceuticals to provide some degree of clarity between different products, these labels must be read by a healthcare worker to ensure that the correct pharmaceutical in a proper concentration or dosage is loaded into the delivery device for administration to a specific patient. Often times, reading these labels can be difficult and time consuming, and human error in doing the same can result in administration of an incorrect pharmaceutical, or the correct pharmaceutical in a wrong concentration or dosage, to the patient. Further, once the pharmaceutical has been removed from the container or vial, the labels do not assist the healthcare workers in identifying the contents in the delivery device or in distinguishing between delivery devices which have been loaded with pharmaceuticals having similar appearances, or delivery devices which have been loaded with the same pharmaceutical in different concentrations or dosages and then set aside before use. In addition, once the pharmaceutical has been removed from the container, the labels do not identify if a certain delivery device is intended for pharmaceutical administration to a specific patient, particularly when the patient is one of a number of patients each having a unique need for administration of a pharmaceutical. To that end, there remains a significant potential for error associated with loading and subsequently administering a pharmaceutical to a patient with the delivery device. Thus, there is a need for additional contributions in this area of technology.

One embodiment of the present application is directed to a system that includes a delivery device, a container, and a tag coupled to the container and configured to store information related to contents of the container. The delivery device is engageable with the tag and at least a portion of the contents of the container are transferrable from the container to the delivery device following its engagement with the tag. The tag is removable from the container in engagement with the delivery device such that the delivery device carries the tag following its removal from the container. In one aspect of this embodiment, a frangible member is coupled to and extends between the tag and the container, and the tag is removable from the container by the delivery device upon breakage of the frangible member. Still, other forms for releasably coupling the tag to the container such that the tag is carried by the delivery device upon its removal from the container are also possible. In one non-limiting form, the system is used for providing and administering a pharmaceutical to a patient, although use of the system in connection with the performance of other activities and for other purposes is also contemplated.

Another embodiment of the present application is a unique system for maintaining the identification of contents removed from a container. Other embodiments include unique methods, systems, devices, kits, assemblies, equipment, and/or apparatus related to readily identifying the contents of a delivery device which have been transferred thereto from a separate container.

Further embodiments, forms, features, aspects, benefits, objects, and advantages of the present application shall become apparent from the detailed description and figures provided herewith.

DETAILED DESCRIPTION OF REPRESENTATIVE EMBODIMENTS

Figure 1:
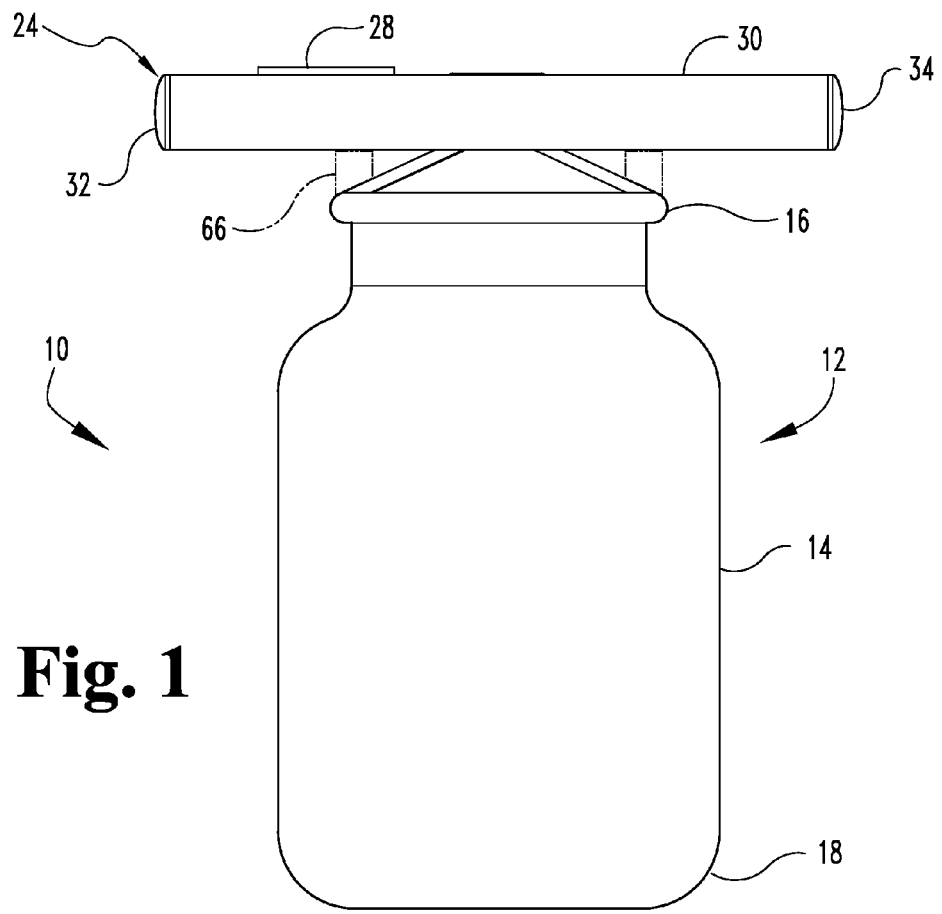
FIG. 1 is a side plan view of an assembly including a transferable identification tag removably coupled with a container.

While the present application can take many different forms, for the purpose of promoting an understanding of the principles of the application, reference will now be made to the embodiments illustrated in the drawings and specific language will be used to describe the same. It will nevertheless be understood that no limitation of the scope of the application is thereby intended. Any alterations and further modifications of the described embodiments, and any further applications of the principles of the application as described herein are contemplated as would normally occur to one skilled in the art to which the application relates.

One embodiment of the present application is directed to a system that includes a delivery device, a container, and a tag coupled to the container and configured to store information related to contents of the container. The delivery device is engageable with the tag and at least a portion of the contents of the container are transferrable from the container to the delivery device following its engagement with the tag. The tag is removable from the container in engagement with the delivery device such that the delivery device carries the tag following its removal from the container. In one aspect of this embodiment, a frangible member is coupled to and extends between the tag and the container, and the tag is removable from the container by the delivery device upon breakage of the frangible member. Still, other forms for releasably coupling the tag to the container such that the tag is carried by the delivery device upon its removal from the container are also possible.

Figure 2:
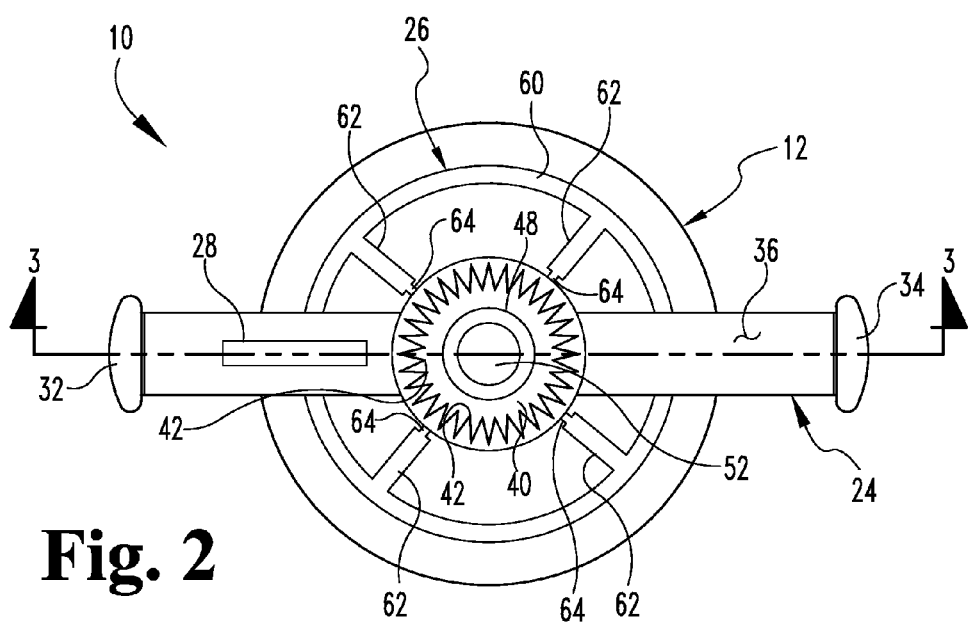
FIG. 2 is a top plan view of the assembly illustrated in FIG. 1.
Figure 3:
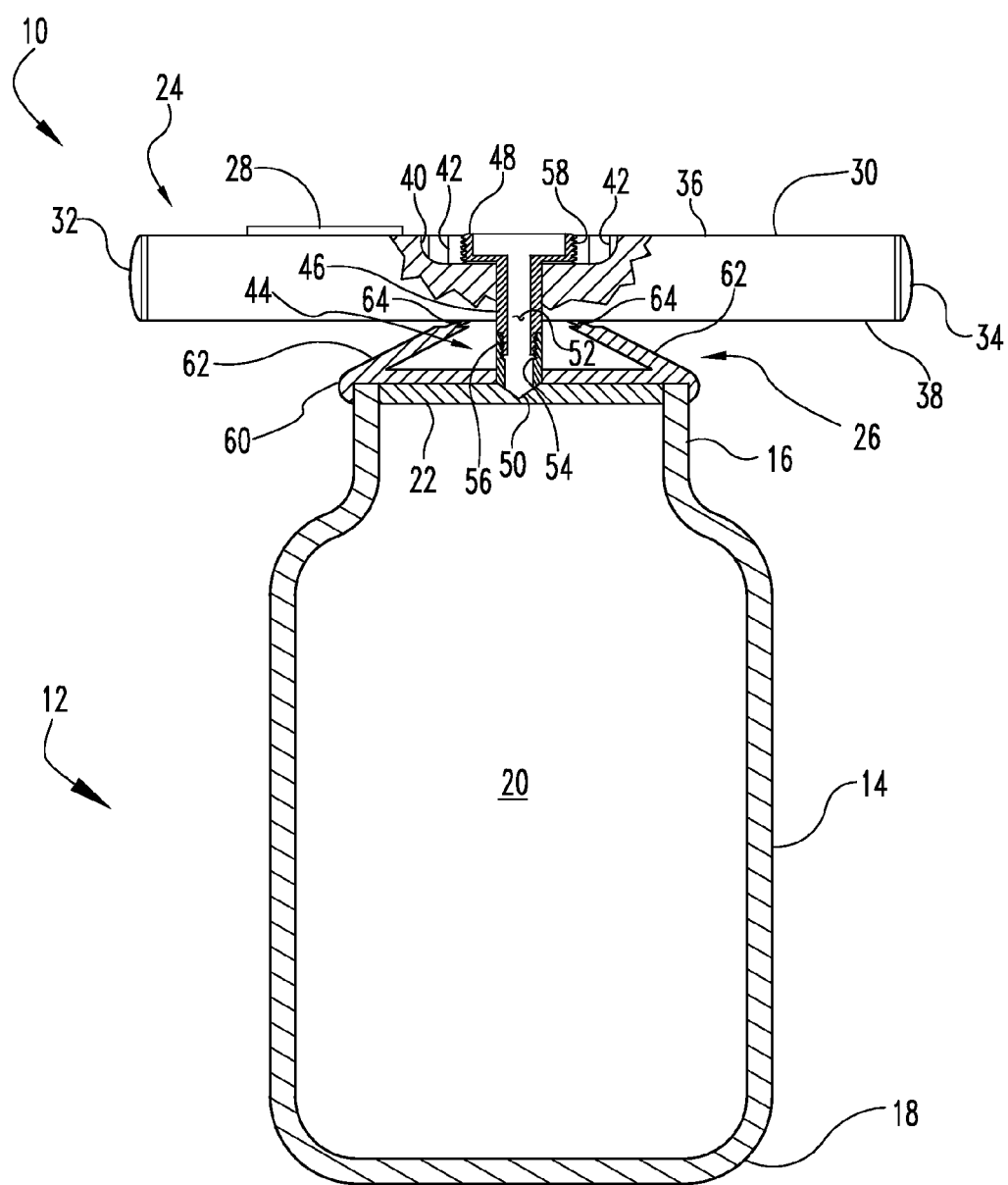
FIG. 3 is a section view of the assembly illustrated in FIG. 1 taken along view line 3-3 of FIG. 2.

Referring collectively to FIGS. 1-3, there is illustrated one embodiment of an assembly 10 including an identification tag removably or releasably coupled to a container. More particularly, assembly 10 includes a container 12 that includes an elongated body 14 extending between a proximal, dispensing end 16 and a distal end 18. Elongated body 14 also includes an internal chamber or receptacle 20 which can be used to store one or more types of products or materials. In one or more forms, container 12 may be a(n) bottle, pouch, ampoule, vial or a bag, just to name a few possibilities. Additionally, while not illustrated, assembly 12 may be provided in packaging to protect it during shipping and handling. In one non-limiting form, container 12 is configured to store one or more fluids or semi-solid materials in internal chamber 20 and to subsequently facilitate their withdrawal from internal chamber 20. In one particular form, container 12 is configured to store a pharmaceutical in internal chamber 20. In one particular aspect of this form, the pharmaceutical stored in internal chamber 20 of container 12 is provided in a concentration and quantity that corresponds to a single dosage intended to be administered to a specific patient or a patient in a class of patients. Container 12 also includes a seal or membrane 22 which seals or encloses proximal, dispensing end 16 but can be penetrated to facilitate withdrawal of contents stored in internal chamber 20, further details of which will be provided below.

Assembly 10 also includes an identification tag 24 that is configured to store information related to contents of container 12 and is releasably coupled with container 12 by a frangible member 26. Identification tag 24 includes an identifier 28 which, in the illustrated form, is of a machine-readable and re-writable format operable to store information related to, inter alia, the contents of container 12. In one form, identifier 28 is a radio frequency identification (RFID) tag that includes an RF driver circuit and a coil antenna. The RF driver circuit generally includes a processor and memory and is operable to transmit and receive information to and from an RF reader/writer upon each interaction with the RF reader/writer. In this manner, data may be stored into and read from identifier 28 at different times and at different locations. In one form, the RF circuitry may be configured as a passive RF transponder that is energized by an external stimulation or excitation signal from an RF reader/writer that is received by the coil antenna. In response to being energized by a stimulation signal, the RF circuitry transmits and receives information to and from the RF reader with the coil antenna in a modulated RF format. In another form, the RF circuitry may be selectively or permanently active in nature, having its own internal power source. For such an alternative, power need not be derived from an external stimulus signal. Indeed, the RF circuitry could initiate communication instead. In yet another alternative form, the RF circuitry may include both active and passive circuits. Still, in other non-illustrated forms, it is contemplated that identifier 28 could include a barcode format, or could be provided in the form of a label, stamp or other marker that includes information related to the contents of container 12. In addition, it is also contemplated that identification 24 could be provided with a label stamp, or other marker that includes information related to the contents of container 12 in combination with identifier 28.

Identifier 28 may be attached to identification tag 24 in any suitable manner. A few non-limiting examples for attaching identifier 28 to identification tag 24 include one or more of pinning, tacking, gluing and adhering, just to name a few possibilities. Still, in another non-illustrated embodiment, identifier 28 may be attached to another tag which is coupled to identification tag 24. In one form of this embedment, a coupling element, such as a ring, cable or wire including opposite ends which are releasably engageable with one another, extends through apertures in the tag and identification tag 24 to couple the tag with identification tag 24. In one aspect of this form, the ends of the coupling element can be disengaged to allow for removal of the tag from identification tag 24 as appropriate. In yet another non-illustrated embodiment, the tag carrying identifier 28 is formed of a resilient, flexible material that includes engaging members structured to deflect away from one another to facilitate a "snap-on" type of coupling with identification tag 24. In other non-illustrated embodiments, it is contemplated that the tag carrying identifier 28 may coupled with identification tag 24 by one or more adhesives, ties, cables, tethers, clamps, clasps, buckles, hooks or other types of fasteners and coupling arrangements, just to name a few possibilities.

Identification tag 24 also includes a body portion 30 on which identifier 28 is positioned. Body portion 30 extends between lateral sides 32, 34 and includes a proximal surface 36 and an opposite distal surface 38 facing proximal, dispensing end 16 of container 12. Body portion 30 includes a recessed portion 40 which is formed in proximal surface 36 and includes a number of radially arranged and inwardly extending ridges or teeth 42 (only a few of which have been identified to preserve clarity). Identification tag 24 also includes a cannula or tubular member 44 having an elongate body 46 extending between a proximal end 48 and an opposite pointed distal end 50. An elongate passage 52 extends between and opens at proximal and distal ends 48, 50 of elongate body 46. In addition, in the illustrated form, distal end 50 includes an internally threaded portion 54 which cooperates with an externally threaded portion 56 on elongate body 46 such that distal end 50 is releasably coupled with elongate body 46. However, it should be understood that forms in which the internally and externally threaded portions 54, 56 are reversed or in which distal end 50 is integrally formed with elongate body 46 are also possible.

As illustrated in FIG. 3 for example, proximal end 48 of cannula 44 includes external threading 58 configured to engage with internal threading on a delivery device, further details of which will be provided below in connection with FIGS. 4 and 5. In addition, a space extends around proximal end 48 of cannula 44 in recessed portion 40 to allow distal displacement of a portion of the delivery device to facilitate engagement of the delivery device with proximal end 48.

As indicated above, identification tag 24 is releasably coupled to container 12 by a frangible member 26. Frangible member 26 includes a distal portion 60 from which a plurality of struts 62 extend to identification tag 24. Distal portion 60 is further structured to engage with container 12 at or adjacent to proximal, dispensing end 16 in any suitable fashion that prevents or substantially eliminates rotation of distal portion 60 relative to container 12, non-limiting examples of which include crimping, adhering or fusing, just to provide a few possibilities. In one non-illustrated form, distal portion 60 may have a solid but penetratable configuration that extends across proximal, dispensing end 16 to provide a seal of internal chamber 20 in addition to or in lieu of seal 22. While not previously discussed, it should be understood that struts 62 can be engaged with identification tag 24 in any suitable fashion, or could be integrally formed with identification tag 24. Each of struts 62 includes a predefined weakened portion 64 positioned adjacent to identification tag 24 and at which each of struts 62 is broken upon sufficient force applied by rotation of identification tag 24 relative to container 12. Similarly, it should be understood that, in the forms illustrated in FIGS. 1-3, identification tag 24 can be rotated relative to container 12 in order to break frangible member 26 and allow identification tag 24 to be removed from container 12. In this arrangement, all or a substantial portion of struts 62 will remain intact with distal portion 60 coupled to container 12 following removal of identification tag 24.

In addition, struts 62 normally bias or position identification away from container 12 such that distal end 50 of cannula 44 is only initially engaged with seal 22, although forms in which distal end 50 is entirely disengaged from seal 22 when identification tag 24 is spaced from container 12 are possible. In this arrangement, it should be understood that internal chamber 20 remains sealed until identification tag 24 is distally displaced from its normal position relative to container 12 in order to remove contents stored in internal chamber 20. More particularly, each of struts 62 includes a deformable or compressible configuration structured to facilitate distal displacement of identification tag 24 toward container 12 upon application of sufficient force to identification tag 24. Notwithstanding the deformable or compressible nature of struts 62, it should be understood that struts 62 can be provided with sufficient rigidity that prevents distal displacement of identification tag 24 toward container 12 during normal shipping and handling until it is desired to remove the contents stored in internal chamber 20. Additionally or alternatively, a spacing member 66 can be removably positioned between identification tag 24 and container 12 in order to prevent distal displacement of identification tag 24 toward container 12 until removal of the contents of container 12 is desired.

Upon distal displacement of identification tag 24 toward container 12, distal end 50 of cannula 44 penetrates seal 22 and becomes positioned in communication with internal chamber 20 such that the contents of container 12 can be removed through identification tag 24 to a delivery device by passage through elongate passage 52 of cannula 44. In one form, it is contemplated that seal 22 is formed of a compressible material, such as rubber or silicone to provide a few non-limiting examples, and includes an orifice that is normally closed to prevent release or contamination of the contents stored in internal chamber 20. However, given the compressible nature of the material from which seal 22 is formed in this form, the orifice is expandable upon distal displacement of pointed distal end 50 of cannula 44 therethrough to facilitate positioning of distal end 50 into communication with internal chamber 20. In other forms however, it is contemplated that seal 22 may be formed of a frangible material, such as an aluminum or plastic film, that may be punctured by distal end 50 of cannula 44 upon distal displacement of identification tag 24 toward container 12 to facilitate positioning of distal end 50 of cannula 44 in communication with internal chamber 20.

Figure 4:
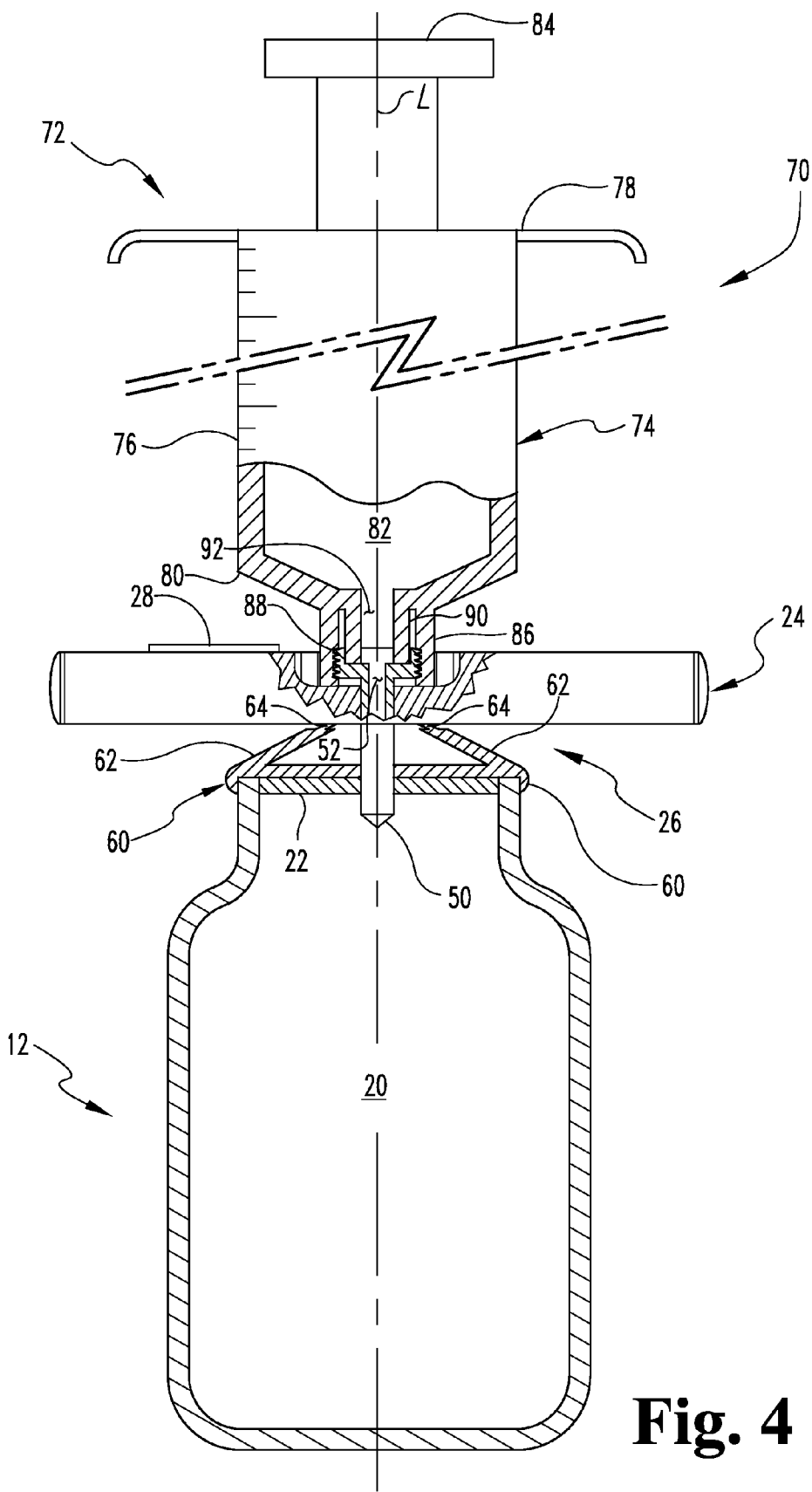
FIG. 4 is a partial section view of a delivery system including the assembly of FIG. 1.
Figure 5:
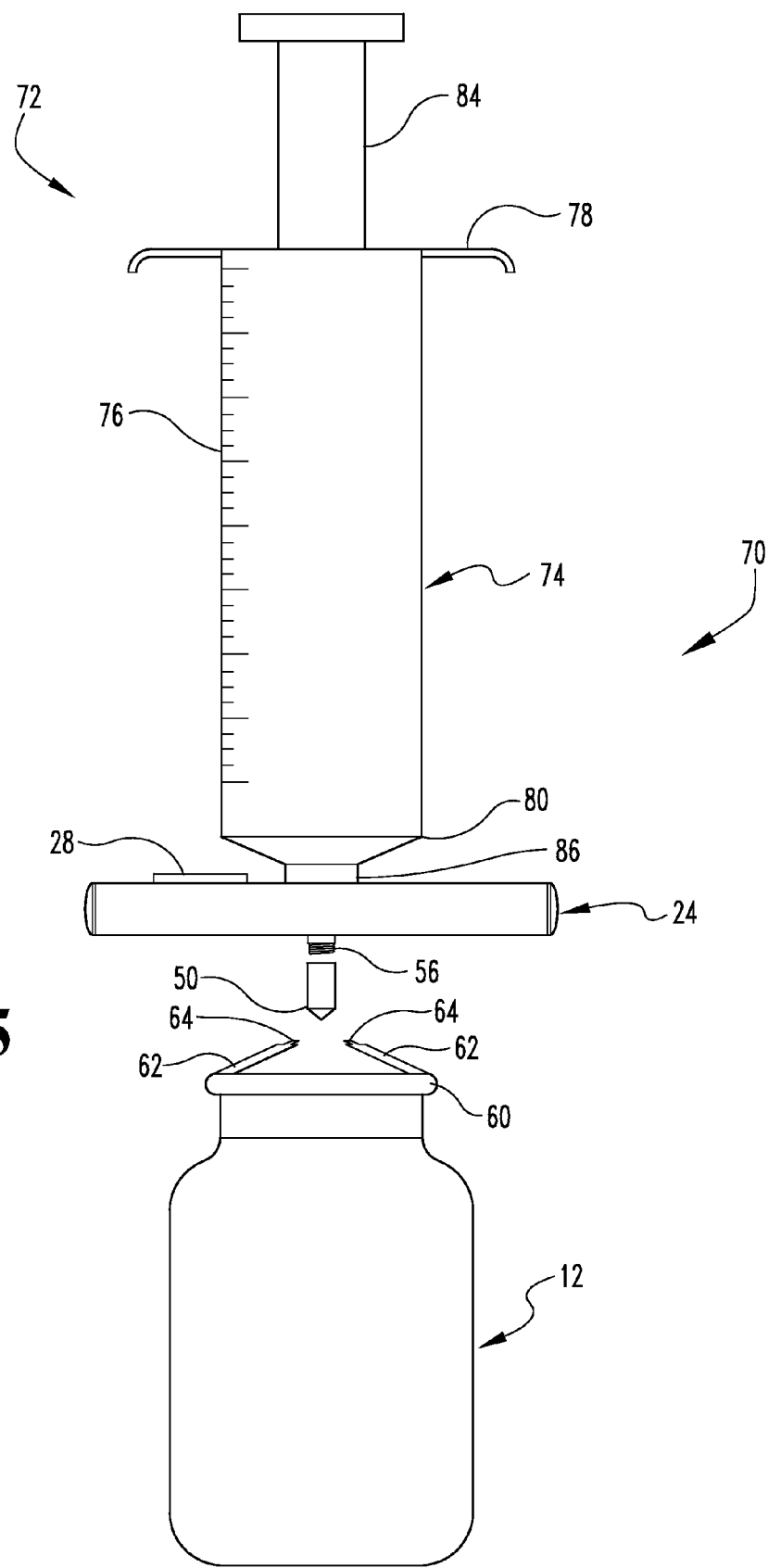
FIG. 5 is a side plan view of the delivery system illustrated in FIG. 4 where the identification tag has been removed from the container.

Turning now to FIGS. 4-5, further details regarding a system 70 including container 12 as previously described and a delivery device 72 will be provided. More particularly, in the illustrated form delivery device 72 is in the form of syringe 74. However, different forms of delivery device 72 in addition to or in lieu of syringe 74 are contemplated. Syringe 74 includes a barrel 76 extending along a longitudinal axis L between a proximal end 78 and a distal end 80 and defining an internal chamber 82. Syringe 74 also includes a plunger 84 which engages with a radial opening (not shown) in proximal end 78 and is longitudinally translatable relative to barrel 76. Opposite plunger 84, syringe 74 includes a distal engaging portion 86 structured to engage with identification tag 24. More specifically, distal engaging portion 86 includes an internally threaded portion 88 which extends around a tubular member 90 having an elongated passage 92 extending in communication with internal chamber 82. As would be appreciated by those skilled in the art, plunger 84 may be translated in a first direction relative to barrel 76 to load internal chamber 82 with a material, and in a second direction relative to barrel 76 to discharge the material from internal chamber 82. While not previously indicated, it is contemplated that syringe 74 may include one or more features in addition to or in lieu of those described herein. Additionally, syringe 74 may be provided in alternative configurations, as would be appreciated by those skilled in the art.

Syringe 74 is engaged with identification tag 24 by engaging internally threaded portion 88 of distal engaging portion 86 with external threading 58 on proximal end 48 of cannula 44 as illustrated in FIG. 4 for example. In this arrangement, a portion of distal engaging portion 86 is positioned in the space between proximal portion 48 and recessed portion 40 such that distal engaging portion 86 is engaged by teeth 42. While not previously discussed, it should be understood that teeth 42 can be provided with an arrangement that allows syringe 74 to be rotated in a first direction into engagement with identification tag 24 but prevents rotation of syringe 74 in an opposite second direction to prevent disengagement of syringe 74 from identification tag 24. For example, the angle of one or more of teeth 42 relative to longitudinal axis L could be deviated in a manner that only allows rotation of syringe 74 in a single direction relative to identification tag 24. Additionally or alternatively, it is contemplated that other configurations of identification tag 24 could be provided that selectively prevent disengagement of syringe 74 such that syringe 74 and identification 24 could be disengaged if desired.

In the illustrated form, a portion of tubular member 90 is positioned in cannula 44 such that elongated passages 52, 92 are in communication with one another. However, in other non-illustrated forms, it should be understood that tubular member 90 may be proximally displaced from cannula 44 when syringe 74 is engaged with identification tag 24. Still, forms in which tubular member 90 is omitted from distal engaging portion 86 are also possible. While not previously discussed, it should also be understood that one or both of internally threaded portion 88 and external threading 58 could be provided with a lubricant to facilitate engagement of syringe 74 with identification tag 24 in a manner that keeps torsional forces below the breaking point of frangible member 26 until syringe 74 is fully engaged with identification tag 24 and at least a portion of the contents of container 12 have been transferred to syringe 74. Additionally or alternatively, it is contemplated that identification tag 24 could be sized and configured for gripping by a user of syringe 74 such that it may be held as it is engaged with syringe 74 to stabilize frangible member 26 from breaking.

As illustrated in FIG. 4 for example, identification tag 24 has been distally displaced such that distal end 50 of cannula 44 is positioned into communication with internal chamber 20 of container 12. In this arrangement, at least a portion of the contents of internal chamber 20 can be withdrawn from container 12 through cannula 44 and tubular member 90 into internal chamber 82 of syringe 74. Once a desired portion of the contents of container 12 have been transferred to syringe 74, identification tag 24 can optionally be proximally displaced to remove distal end 50 from internal chamber 20, and syringe 74 and identification 24 engaged thereby can be rotated relative to container 12 to break frangible member 26 and disengage identification tag 24 from container 12. Similarly, in this arrangement, identification tag 24 is carried by syringe 74 following its removal from container 12. As a corollary, by way of identifier 28 of identification tag 24, syringe 74 seamlessly includes information related to the contents which have been transferred to it from container 12, and a user of syringe 74 can readily identify its contents by reading identifier 28.

Once identification tag 24 has been removed from container 12, the contents of syringe 74 can be used at any appropriate time and in any appropriate manner. However, before use, identifier 28 can be read to ensure that the contents of syringe 74 will be used in an intended manner. As indicated above, in one non-limiting form container 12 can be used to store a pharmaceutical product. In this form, once at least a portion of the pharmaceutical has been removed from container 12, a healthcare worker can use syringe 74 to administer the pharmaceutical to a patient. In one form, the amount and concentration of the pharmaceutical stored in container 12 corresponds to a single dosage intended for a specific patient or a patient in a class of patients. In these forms, the entire amount of the pharmaceutical stored in container 12 is transferred to syringe 74, and the need for the healthcare worker to measure the amount of pharmaceutical being removed from container 12 is eliminated. Before the pharmaceutical in syringe 74 is administered to the patient, identifier 28 can be read by the healthcare worker to confirm the correct pharmaceutical and dosage is being administered to the targeted or intended patient. Once this confirmation has been determined, the pharmaceutical may be directly administered to the patient by engaging distal end 50 of cannula 44 with a catheter, injection port, or other access site and discharging the pharmaceutical from syringe 74. As an alternative, distal end 50 can be removed from cannula 40, and a needle (not shown) can be engaged therewith to facilitate injection of the pharmaceutical instramuscularly or subcutaneously, amongst other possibilities, from syringe 74. Further details regarding one non-limiting system in which system 70 may be used for administering a pharmaceutical to a patient are provided below in connection with FIGS. 8-10.

Following administration of the pharmaceutical, syringe 74 and identification tag 24 can be disposed together, although forms in which one or both of syringe 74 and identification tag 24 are reusable are also contemplated. For example, in one form, identification tag 24 may be removed from syringe 74 after the pharmaceutical has been administered therefrom. In this manner, identification tag 24 may be reused and coupled with another container 12 which contains a new pharmaceutical or medical product. Similarly, identifier 28 can be rewritten to store information regarding the new pharmaceutical or medical product.

Figure 6:
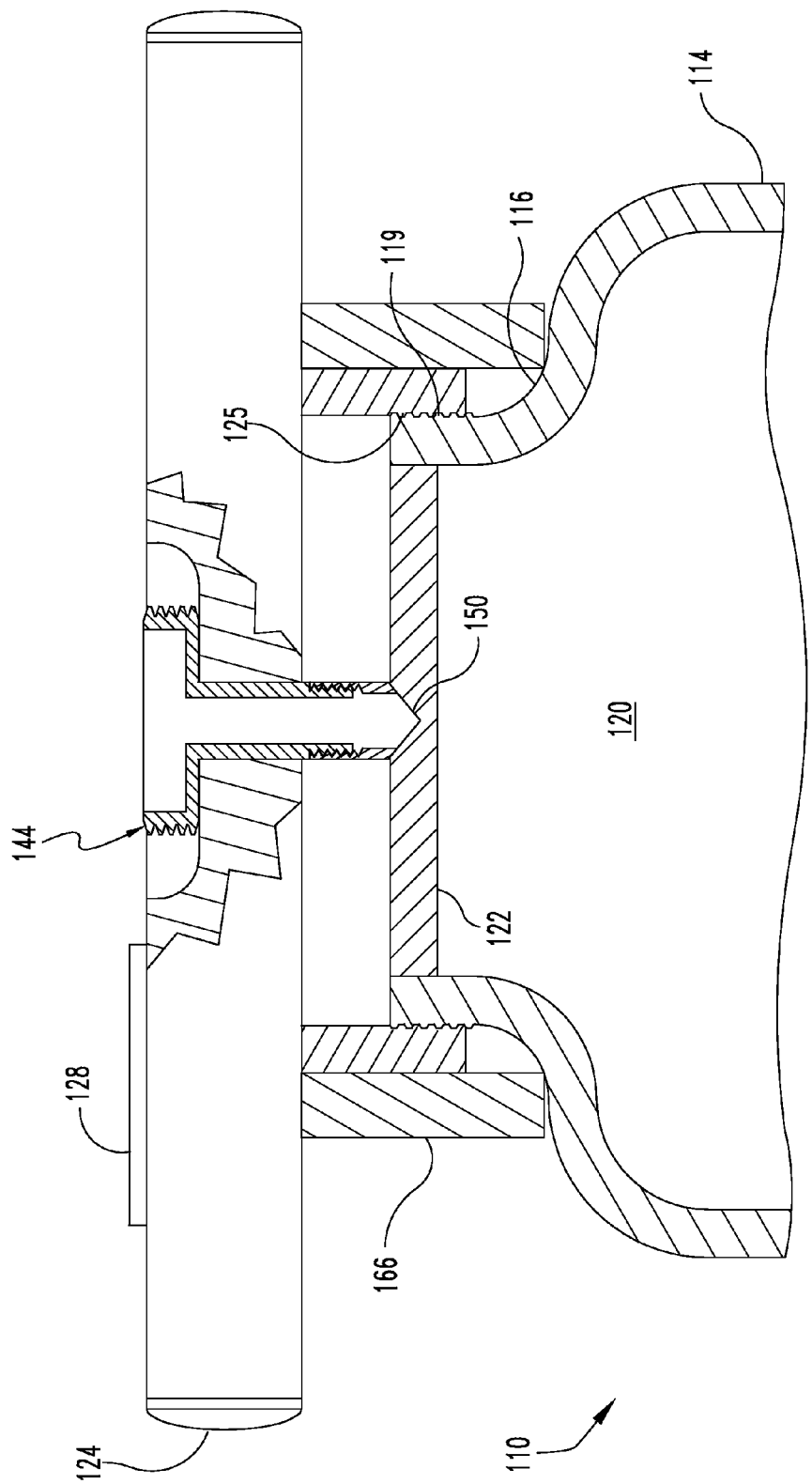
FIG. 6 is a section view of an alternative embodiment assembly including a transferable identification tag removably coupled with a container.

Referring now to FIG. 6, further details regarding an alternative embodiment assembly 110 will be provided. Assembly 110 includes container 112 that is similar to container 12 such that much of the description of container 12 provided above is also applicable to container 112. Container 112 includes an elongated body 114 extending between a proximal, dispensing end 116 and a distal end 118. Elongated body 114 also includes an internal chamber or receptacle 120 which can be used to store one or more types of products or materials. Proximal, dispensing end 116 includes an externally threaded portion 119 and a seal or membrane 122 which seals or encloses proximal, dispensing end 116 but can be penetrated to facilitate withdrawal of contents stored in internal chamber 120.

Assembly 110 also includes an identification tag 124 that is configured to store information related to contents of container 112 and is releasably coupled with container 112. Identification tag 124 includes an identifier 128 which can be configured the same as or substantially similar to identifier 28, and a cannula 144 which can be configured the same as or substantially similar to cannula 44 and to engage with delivery device 72. Identification tag 124 also includes an internally threaded collar 125 configured to engage with externally threaded portion 119 of container 112. Assembly 110 also includes a spacer member 166 removably positioned between identification tag 124 and container 112 such that identification tag 124 is normally spaced from container 112 with distal end 150 of cannula 144 being positioned out of communication with internal chamber 120. However, in other forms, it is contemplated that spacing member 166 could be omitted from assembly 110, and container 112 could be provided with alternative structure for normally spacing identification tag 124 from container 112. Still, forms in which assembly 110 does not include any structure for maintaining spacing of identification tag 124 and container 112 are also possible.

Identification tag 124 may be distally displaced toward container 112 to position distal end 150 of cannula 144 into communication with internal chamber 120 when it is desired to remove contents from container 112. More particularly, once spacing member 166 is removed, identification tag 124 can be rotated and threadingly advanced along container 112 until distal end 150 of cannula 144 is positioned into communication with internal chamber 112. In one form, it is contemplated that advancing rotation of identification tag 124 is performed during or after engagement of identification tag 124 with delivery device 72. In this form, once the desired portion of the contents in container 112 have been transferred to delivery device 72, identification tag 124 can be rotated relative to container 112 until it is disengaged from container 112 such that is subsequently carried by delivery device 72 as discussed above.

In another form however, it is contemplated that identification tag 124 could be rotated independently of delivery device 72 until distal end 150 of cannula 144 is positioned into communication with internal chamber 120, followed by engagement with delivery device 72. In one aspect of this form, it contemplated that the threaded arrangement between delivery device 72 and identification tag 124 could be provided with a first orientation, e.g., a right-hand thread, while the threaded arrangement between identification tag 124 and container 112 could be provided with a second, opposite orientation, e.g., a left-hand thread, such that identification tag 124 could be removed from container 112 by rotating delivery device 72 and tag 124 relative to container 112 following transfer of its contents into delivery device 72.

Figure 7:
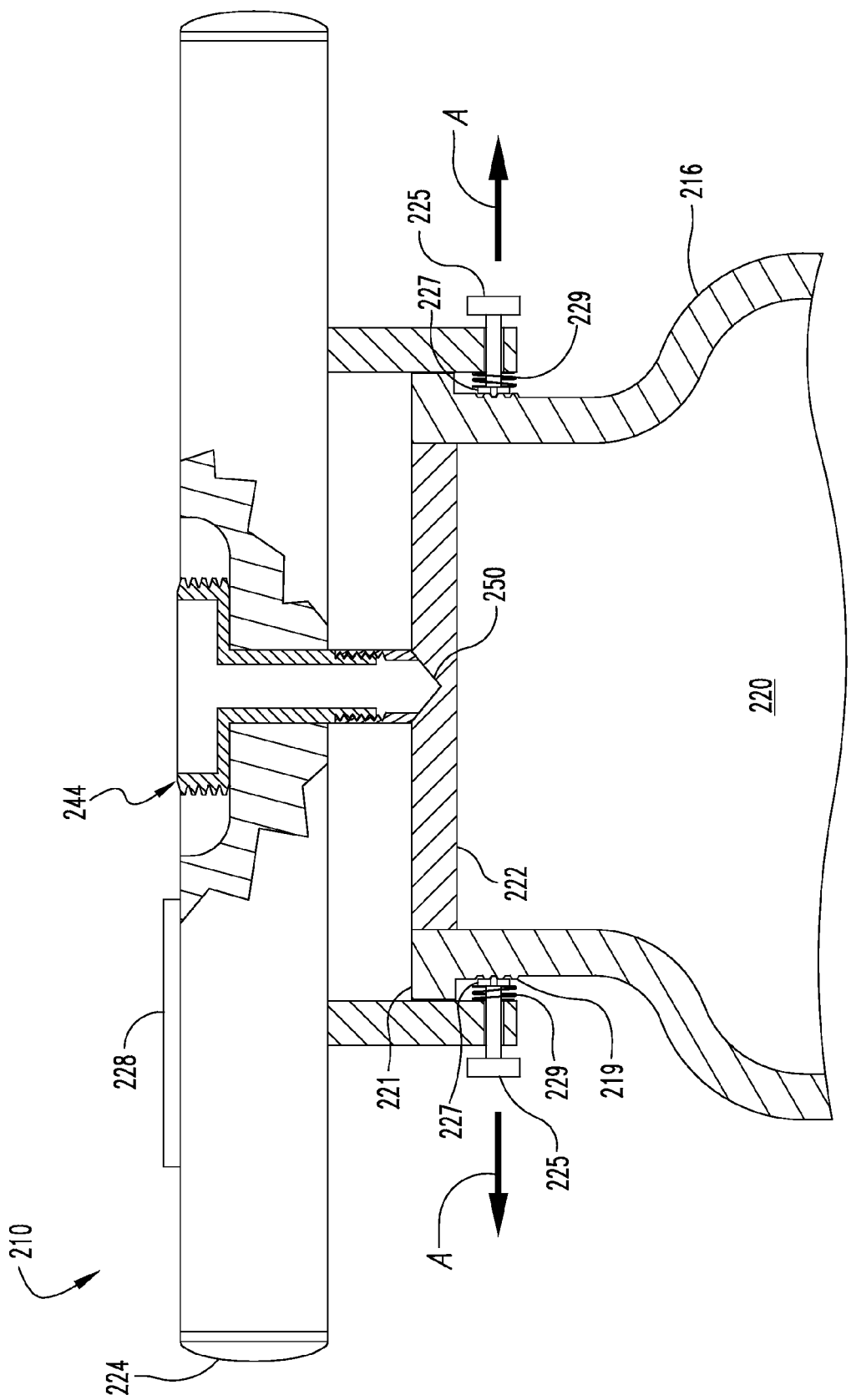
FIG. 7 is a section view of another alternative embodiment assembly including a transferable identification tag removably coupled with a container.

Turning now to FIG. 7, further details regarding another alternative embodiment assembly 210 will be provided. Assembly 210 includes container 212 that is similar to container 12 such that much of the description of container 12 provided above is also applicable to container 212. Container 212 includes an elongated body 214 extending between a proximal, dispensing end 216 and a distal end 218. Elongated body 214 also includes an internal chamber or receptacle 220 which can be used to store one or more types of products or materials. Proximal, dispensing end 216 includes an externally threaded portion 219 and a flange 221 extending laterally beyond externally threaded portion 219. In addition, a seal or membrane 222 seals or encloses proximal, dispensing end 216 but can be penetrated to facilitate withdrawal of contents stored in internal chamber 220.

Assembly 210 also includes an identification tag 224 that is configured to store information related to contents of container 212 and is releasably coupled with container 212. Identification tag 224 includes an identifier 228 which can be configured the same as or substantially similar to identifier 28, and a cannula 244 which can be configured the same as or substantially similar to cannula 44 and to engage with delivery device 72. Identification tag 224 also includes a pair of opposing pins 225 each of which includes an end 227 normally biased by a biasing member 224 into engagement with externally threaded portion 219 of container 212. Assembly 210 may optionally include a spacer member (not shown) removably positioned between identification tag 224 and container 212 such that identification tag 224 is normally spaced from container 212 with distal end 250 of cannula 244 being positioned out of communication with internal chamber 220. However, in other forms, it is contemplated that container 212 could be provided with alternative structure for normally spacing identification tag 224 from container 212. Still, forms in which assembly 210 does not include any structure for maintaining spacing of identification tag 224 and container 212 are also possible.

Identification tag 224 may be distally displaced toward container 212 to position distal end 250 of cannula 244 into communication with internal chamber 220 when it is desired to remove contents from container 212. More particularly, once any spacing structure is removed (if present), identification tag 224 can be engaged and rotated by delivery device 72 to be threadingly advanced along container 212 until distal end 250 of cannula 244 is positioned into communication with internal chamber 212. Once the desired portion of the contents in container 212 have been transferred to delivery device 72, pins 225 can be moved away from one another as indicated by directional arrows A in FIG. 7, which in turn disengages ends 227 from externally threaded portion 219 of container 212 and allows identification tag 224 to be removed from container 212. Similarly, in this arrangement identification tag 224 is carried by delivery device 72 following its removal from container 212. Still, it should be appreciated that other arrangements for releasably coupling an identification tag with a container are also possible.

Figure 8:
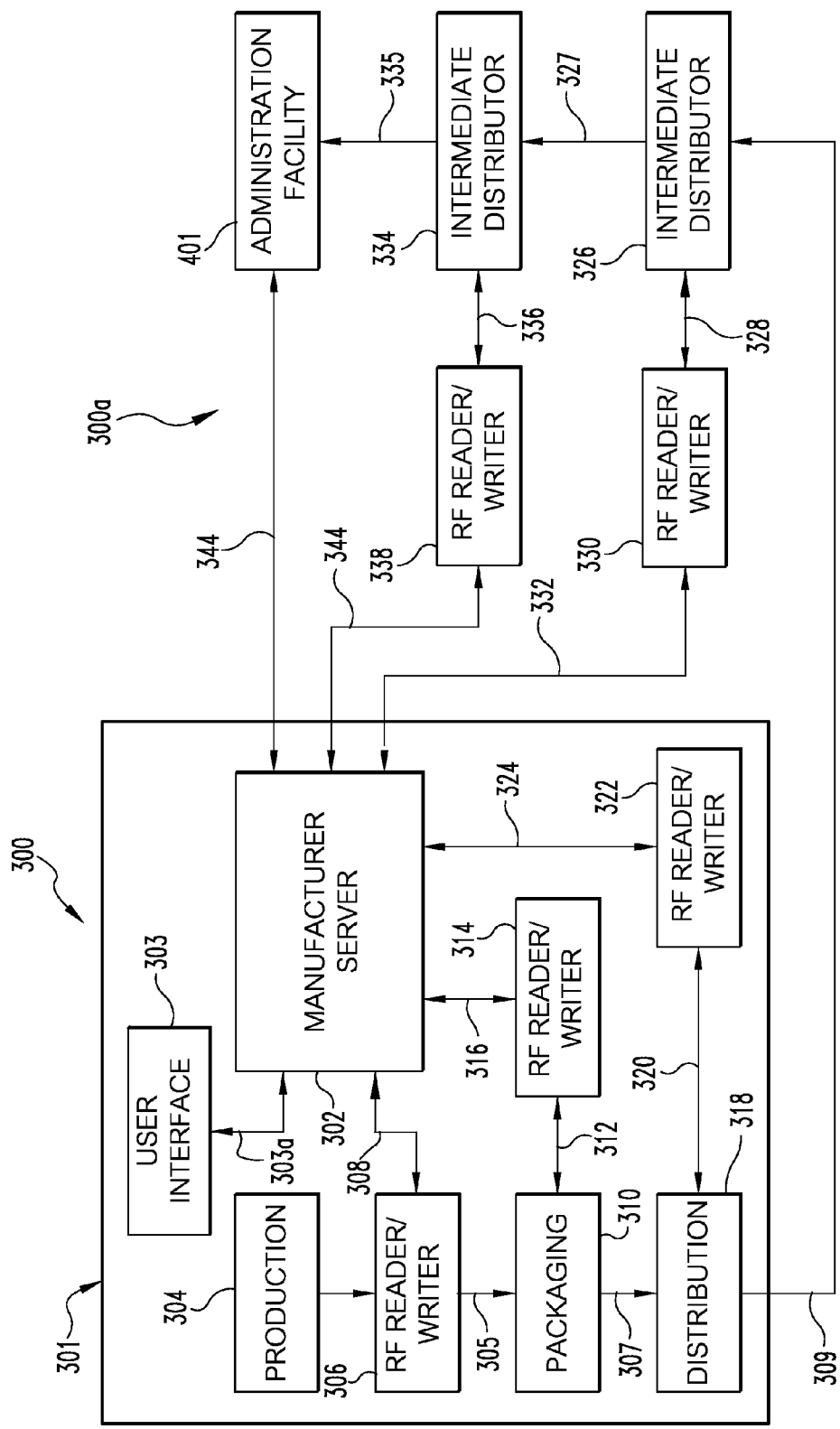
FIG. 8 is a schematic illustration of one portion of a system involving the assembly of FIG. 1 for providing a pharmaceutical to a patient.
Figure 9:
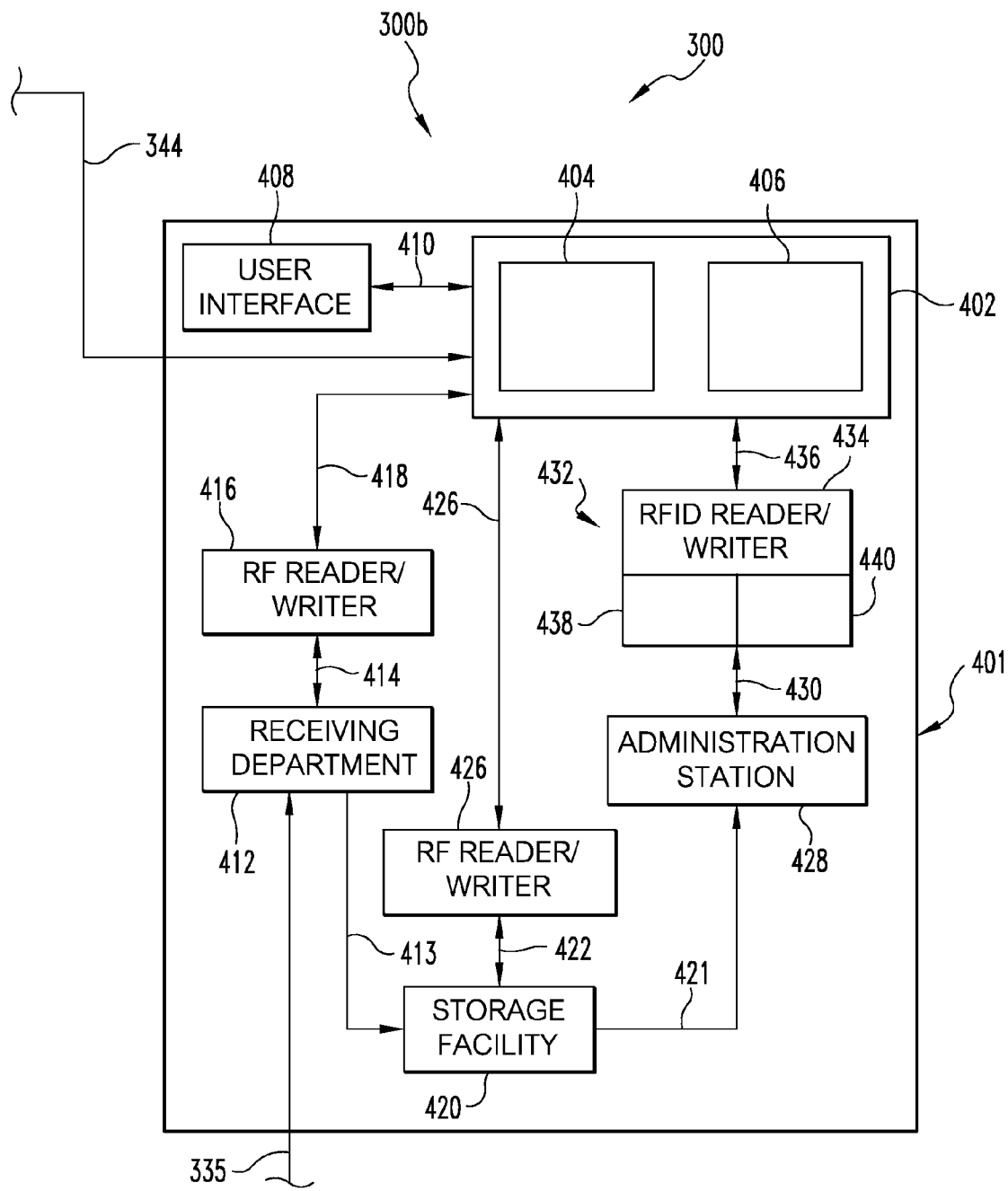
FIG. 9 is a schematic illustration of another portion of a system involving the assembly of FIG. 1 for providing the pharmaceutical to the patient.

Referring now generally to FIGS. 8 and 9, there is schematically illustrated a system 300 for providing a pharmaceutical to a patient utilizing assembly 10 and delivery device 72, although forms in which assembly 110 or 210 could be utilized are also possible. In addition, it should be appreciated that any one or more of assemblies 10, 110, 210 and delivery device 72 could be used in an alternatively arranged system for providing a pharmaceutical to a patient or for purposes other than providing a pharmaceutical to a patient. Further details regarding system 300 may be found in U.S. Patent Publication No. 2010/00366678 to Bray, the contents of which are incorporated herein by reference in their entirety.

For the sake of clarity, system 300 has been split into interconnected sections 300a and 300b in FIGS. 8 and 9, respectively. For the purposes of the instant description, it should be appreciated that section 300a generally illustrates the manufacture/production and distribution of the pharmaceutical to an administration facility 401, while section 300b generally illustrates the tracking and administering of the pharmaceutical to the patient within administration facility 401. However, it should be appreciated that system 300, as a whole, is responsible for performing each of these functions. Moreover, as will be explained further below, system 300 can be configured to allow a user to track and locate the pharmaceutical from the point of production to the point of administration and at each intermediate stage between production and administration to the patient. While system 300 is described herein with respect to a single pharmaceutical product, it should be appreciated that system 300 can be used for providing numerous pharmaceuticals to a variety of patients at a variety of administration facilities.

In FIG. 8, section 300a of system 300 illustrates a supply facility 301, such as a manufacturer, which includes a server 302, a production department 304, a packaging department 310, a distribution department 318 and RF readers/writers 306, 314, 322. It should be appreciated that supply facility 301 may include one or more elements in addition to or in lieu of those illustrated in FIG. 8. Moreover, it is contemplated that one or more of departments 304, 310, 318 may be provided outside supply facility 301 and/or may be excluded entirely from system 300. RF readers/writers 306, 314, 322 are coupled with server 302 through pathways 308, 316, 324, respectively, for bidirectional communication between each respective RF reader/writer 306, 314, 322 and server 302. It is contemplated that pathways 308, 316, 324 may represent one or more of a hard-wired or wireless connection between server 302 and each respective RF reader/writer 306, 314, 322 over a network such as a Local Area Network (LAN), Municipal Area Network (MAN), Wide Area Network (WAN), a combination of these, or such other network arrangement as would occur to those skilled in the art. In one form, the network is of a WAN type including the internet.

Server 302 is generally operable to store information regarding the manufacture, distribution and administration of a pharmaceutical product, provide such information to a user, and control one or more operating parameters of system 300. However, it should be appreciated that other operating functions of server 302 are contemplated by the present application. In one form, server 102 is a computer that includes one or more processors or CPUs and one or more types of memory. Each processor may be comprised of one or more components configured as a single unit. When of a multi-component form, a processor may have one or more components located remotely relative to the others. One or more components of each processor may be of the electronic variety defining digital circuitry, analog circuitry, or both. In one embodiment, each processor is of a conventional, integrated circuit microprocessor arrangement.

Each memory is one form of a computer-readable device. Each memory may include one or more types of solid-state electronic memory, magnetic memory, or optical memory, just to name a few. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, each memory may be volatile, nonvolatile, or a hybrid combination of volatile and nonvolatile varieties.

A user interface 303 is coupled to server 302 via pathway 303a and includes an output providing information from server 302 to a user and one or more user input devices for entering information into server 302 or changing one or more operating parameters of system 300. When included, the output can be a display of a Cathode Ray Tube (CRT) type, Liquid Crystal Display (LCD) type, plasma type, Organic Light Emitting Diode (OLED) type, a printer, or other types as would occur to those skilled in the art. Moreover, the user input devices may include one or more of a keyboard, mouse, track ball, light pen, and/or microtelecommunicator, to name just a few representative examples.

Production department 304 is generally operable to produce and provide a pharmaceutical in container 12 of assembly 10. Supply facility 301 may manufacture assembly 10 and the pharmaceutical and fill container 12 with the pharmaceutical at production department 304. Alternatively, supply facility 301 only manufactures one of assembly 10 and the pharmaceutical or may not manufacture either of assembly 10 and the pharmaceutical. Instead, supply facility has one or both of the pharmaceutical and assembly 10 supplied to it and then fills container 12 with the pharmaceutical at production department 304. The pharmaceutical may be any one of a variety of liquid drug products administered to a patient. As indicated above, in one form, it is contemplated that the pharmaceutical may be provided in container 12 in an amount and concentration that is intended to correspond to a single dosage to specific patient or a patient in a class of patients. More particularly, the appropriate relationship between volume and concentration of the pharmaceutical which is necessary for a single dosage to a specific patient or a patient in a class of patients may be determined and dispensed into container 12. For example, in one form it is contemplated that container 12 may be loaded with the pharmaceutical in a form suitable for single dosage injection to adults instead of children, although other variations and identifications of classes are contemplated. Thus, in one form container 12 includes a single dosage of the pharmaceutical which eliminates the need for a healthcare worker to measure, mix, formulate or otherwise prepare the pharmaceutical.

Each assembly 10 provided by production department 304 includes identification tag 24 having identifier 28 onto which information related to the pharmaceutical can be stored and/or written. As the information is written onto each identifier 28, a unique code is assigned to each and a file based on each unique code is created on server 302 to store information regarding each assembly 10. In one form, it is contemplated that the information stored in each identifier 28 is also stored in the corresponding file on server 302 and vice versa. In this configuration, each time identifier 28 interacts with an RF reader in bidirectional communication with server 302, identifier 28 and its respective file on server 302 are reconciled so that each includes the same information. However, it should be appreciated that identifier 28 or its respective file on server 302 may include information that is unique to it; i.e., such information is not stored on the other of identifier 28 and server 302.

As assembly 10 leaves production department 304, RF reader/writer 306 writes information onto identifier 28. The information written by RF reader/writer 306 and stored on identifier 28 may identify specifications and/or characteristics of the pharmaceutical, including without limitation, any one or more of its name, class, type, concentration, volume, manufacturing date, expiration date, lot number, chemical formula, active ingredient, pharmacology, mechanism of action, targeted disease states/conditions and manufacturer. This information may also identify known adverse drug/drug interactions and contraindications of the pharmaceutical. Where the pharmaceutical is provided in a dosage intended to be administered to a patient falling within a specific class or classes of patients, the information on identifier 28 may also identify the members of the class or classes. For example, it might identify that the pharmaceutical in container 12 should be administered to patients falling within one or more of a certain age, weight, sex or disease state class, just to name a few possibilities. While not previously discussed, it should be appreciated that the information stored onto identifier 28 upon interaction with RF reader/writer 306 may be first added onto server 302 by a user at interface 303 or, alternatively, it is contemplated that one or both of server 302 and RF reader/writer 306 may be automatically updated with information from production department 304 as it provides containers 12. It should be appreciated that a user may utilize interface 303 to continually update the information stored in the file on server 302 associated with identifier 28 such that the information on identifier 28 can be correspondingly updated each time it interacts with an RF reader/writer in communication with server 302. Additionally, it is contemplated that RF reader/writer 306 may be operable to provide identifier 28 with the date and/or time it interacts with RF reader/writer 306.

After identifier 28 has been loaded with the above-described information, assembly 10 is moved to packaging department 310, as indicated by arrow 305. At packaging department 310, assembly 10 may be individually packaged for distribution beyond supply facility 301. Alternatively, a plurality of assemblies 10 could be grouped together and placed in shared packaging. RF reader/writer 314 interacts with identifier 28 of assembly 10 as indicated by communication pathway 312 to provide identifier 28 with the time and/or date at which assembly 10 is received into and leaves from packaging department 310. RF reader/writer 114 is also operable to update any information previously stored on identifier 28 and may write other information, such as a product recall, onto identifier 28. Once properly packaged, assembly 10 is passed along to distribution department 318 as indicated by arrow 307. RF reader/writer 322 associated with distribution department 318 interacts with identifier 28 of assembly 10 as indicated by communication pathway 320 to provide the time and/or date at which assembly 10 is received into and leaves from distribution department 318. RF reader/writer 322 is also operable to update any information previously stored on identifier 28 and may write other information, such as a targeted destination for assembly 10, onto identifier 28. Moreover, in one form, when assembly 10 leaves supply facility 301 server 302 is operable to send a report, such as an email, to the party that ordered assembly 10 and/or to any party or parties that will be involved in the distribution of assembly 10.

It is contemplated that assembly 10 may pass through one or more intermediate distributors, such as warehouses for example, between supply facility 301 and administration facility 401. For example, as illustrated in FIG. 8, assembly 10 passes from supply facility 301 to intermediate distributor 326, as indicated by arrow 319, and from intermediate distributor 326 to intermediate distributor 334, as indicated by arrow 327, before it reaches administration facility 401. Intermediate distributor 326 includes an RF reader/writer 330 which is connected with server 302 via pathway 332 to bidirectionally communicate therewith. RF reader/writer 330 interacts with identifier 28 of assembly 10 as indicated by communication pathway 328 to provide the time and/or date at which assembly 10 is received into and leaves from intermediate distributor 326. RF reader/writer 330 is also operable to update any information previously stored on identifier 28 and may write other information, such as the location of intermediate distributor 326 or the conditions in which assembly 10 is being stored, onto identifier 28. Similar to intermediate distributor 326, intermediate distributor 334 includes an RF reader/writer 338 which is coupled with server 302 via pathway 340 to bidirectionally communicate therewith. RF reader/writer 138 interacts with identifier 28 of assembly 10 as indicated by communication pathway 336 to provide the time and/or date at which assembly 10 is received into and leaves from intermediate distributor 334. RF reader/writer 338 is also operable to update any information previously stored on identifier 28 and may write other information, such as the location of intermediate distributor 334 or the conditions in which assembly 10 is being stored, onto identifier 28. It is contemplated that pathways 332, 340 may represent one or more of a hard-wired or wireless connection between server 302 and RF readers/writers 330, 338 over a network such a Local Area Network (LAN), Municipal Area Network (MAN), Wide Area Network (WAN), a combination of these, or such other network arrangement as would occur to those skilled in the art. In one form, the network is of a WAN type including the internet.

Assembly 10 is delivered to administration facility 401 from intermediate distributor 334 as indicated by arrow 335. Administration facility 401 may be a hospital, pharmacy, nursing home, clinic or physician's office, just to name a few possibilities. In the embodiment illustrated in FIG. 9, administration facility 401 generally includes a management computer 402, a receiving department 412, a storage facility 420, an administration station 428, an administration terminal 432 which includes RF reader/writer 434, and RF readers/writers 416 and 424. However, it should be appreciated that administration facility 401 may include fewer elements or one or more elements in addition to or in lieu of those illustrated and described herein. Administration terminal 432 and RF readers/writers 416, 424 are coupled with management computer 402 through pathways 436, 418 and 426, respectively, for bidirectional communication between management computer 402 and each of respective administration terminal 432 and RF readers/writers 416, 424. Additionally, management computer 402 is coupled with server 302 at supply facility 301 through pathway 344 for bidirectional communication between management computer 402 and server 302. It should be appreciated that management computer 202 can be programmed to only share certain information with server 302. For example, management computer 402 may be configured to prohibit any confidential patient information from being transmitted to server 302 in order to comply with various local, state and federal regulations. Pathways 344, 418, 426, 436 may represent one or more of a hard-wired or wireless connection over a network such a Local Area Network (LAN), Municipal Area Network (MAN), Wide Area Network (WAN), a combination of these, or such other network arrangement as would occur to those skilled in the art. In one form, the network is of a WAN type including the internet.

Management computer 402 includes one or more processors or CPUs and one or more types of memory. Each processor may be comprised of one or more components configured as a single unit. When of a multi-component form, a processor may have one or more components located remotely relative to the others. One or more components of each processor may be of the electronic variety defining digital circuitry, analog circuitry, or both. In one embodiment, each processor is of a conventional, integrated circuit microprocessor arrangement. Each memory is one form of a computer-readable device. Each memory may include one or more types of solid-state electronic memory, magnetic memory, or optical memory, just to name a few. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, each memory may be volatile, nonvolatile, or a hybrid combination of volatile and nonvolatile varieties. As illustrated in FIG. 9, at least a portion of the memory is used for storing patient information in a patient file 404 uniquely associated with a patient of administration facility 401 while another portion of the memory is used for providing a virtual inventory 406 of the pharmaceutical products at administration facility 401. While only one patient file 404 has been illustrated on management computer 402 in FIG. 9, it should be appreciated that management computer 402 is generally operable to create and store a similar file for each patient of facility 401.

A user interface 408 is coupled to management computer 402 via pathway 410 and may include an output providing information from management computer 402 to a user and one or more user input devices for entering information into management computer 402. When included, the output can be a display of a Cathode Ray Tube (CRT) type, Liquid Crystal Display (LCD) type, plasma type, Organic Light Emitting Diode (OLED) type, a printer, or other types as would occur to those skilled in the art. Moreover, the user input devices may include one or more of a keyboard, mouse, track ball, light pen, and/or microtelecommunicator, to name just a few representative examples.

In one form, a user may utilize user interface 408 for entering patient information into patient file 404 saved on management computer 402. More particularly, in one exemplary form, a user may take information related to the patient's medical history from the patient upon the patient's initial visit or admittance to administration facility 401 and enter it at user interface 408 to create patient file 404. The information in patient file 404 may identify one or more of the name, age, sex, height, weight, physician, known allergies, diet restrictions, weight restrictions, emergency contacts, family members, place of employment, insurance company, previous pharmaceutical use, previous illnesses/diseases, previous surgeries, existing pharmaceutical use, existing medical conditions, existing treatment plans and medical condition giving rise to the current treatment of the patient. Additionally, user interface 408 may be used by one or more healthcare workers to enter information into patient file 404 regarding the current treatment of the patient. For example, such information may identify a physician order, such as a prescription, indicating the type and amount of a pharmaceutical which should be administered to the patient along with details identifying the date and/or time when the pharmaceutical should be administered to the patient. It should be appreciated that patient file 404 may be updated to reflect changes regarding the patient's medical history or treatment that may occur during the patient's visit or admittance to administration facility 401 or that might have occurred since the patient's initial visit or admittance to administration facility 401. Thus, patient file 404 has the potential to become an ongoing comprehensive medical file of the patient which includes not only information related to the patient's association with administration facility 401, but also provides an overall detailed medical history for the patient.

When assembly 10 is received in receiving department 412, RF reader/writer 416 interacts with identifier 28 as indicated by communication pathway 414 and the virtual inventory 406 is updated to indicate receipt of assembly 10. In one form, virtual inventory 406 creates a file for assembly 10 based on the unique code assigned to identifier 28 at supply facility 301. The file created on virtual inventory 406 for assembly 10 may store all or part of the information that has been previously written on identifier 28 before assembly 10 is received by administration facility 401. This file may also include an indication as to the current location of assembly 10 within administration facility 401 as well as the time and date when assembly 10 was received by, and is subsequently moved around, administration facility 401. As indicated above, server 302 and management computer 402 bidirectionally communicate with each other through pathway 344. In one configuration, the information on virtual inventory 406 is shared with server 302 and server 302, which identifies the unique code assigned to identifier 28, is updated to reflect receipt of assembly 10 by administration facility 401. More particularly, server 102 may be updated to include the time and/or date when assembly 10 was received by administration facility 401 or is subsequently moved within administration facility 401. In this configuration, server 302 can also provide virtual inventory 406 with updates, such as recall or expiration information for example, that should be written onto identifier 28. Virtual inventory 406 correspondingly provides these updates to RF reader/writer 416 where they are written onto identifier 28. It should be appreciated that virtual inventory 406 can be continually updated each time identifier 28 interacts with an RF reader/writer in administration facility 401 until the pharmaceutical is administered to the patient. Likewise, server 302 may also be correspondingly updated to reflect the location/status of assembly 10. Additionally, server 302 can periodically provide updates regarding the pharmaceutical to virtual inventory 406 which in turn updates identifier 28 each time it interacts with an RF reader/writer at administration facility 401.

In an alternative configuration, management computer 402 may be configured to allow server 302 to directly communicate with administration terminal 432 and RF readers/writers 416, 424 to determine the status/location of assembly 10 and/or provide updates to be stored on identifier 28. Thus, the need for intermediate communication between server 302 and virtual inventory 406 is eliminated. However, server 302 may still communicate with virtual inventory 406 to receive orders for additional pharmaceutical products or the like. In this configuration, it should be appreciated that management computer 402 is still generally operable to filter any confidential information from being passed to server 302.

It is contemplated that assembly 10 may pass through one or more storage facilities within administration facility 401 between receiving department 412 and administration station 428. For example, as illustrated in FIG. 9, assembly 10 passes from receiving department 412 to storage facility 420, as indicated by arrow 413. Storage facility 420 may be, for example, a pharmacy, medication dispensing unit, cart, chest or room, just to name a few possibilities. Storage facility 420 includes an RF reader/writer 424 which interacts with identifier 28 of assembly 10 as indicated by communication pathway 422 to provide the time and/or date at which assembly 10 is received into and leaves from storage facility 420. RF reader/writer 424 is also operable to update any information previously stored on identifier 28 and may write other information, such as the location of storage facility 420 within administration facility 401, onto identifier 28.

Assembly 10 is delivered to administration station 428 from storage facility 420 as indicated by arrow 421. Administration station 428 may be, for example, a pharmacy counter or a patient's bedside or chairside, just to name a few representative possibilities. In the embodiment illustrated in FIG. 9, administration terminal 432 is positioned adjacent to administration station 428. Administration terminal 432 includes RF reader/writer 434 and a user input 438 and an output 440. Output 440 can be a display of a Cathode Ray Tube (CRT) type, Liquid Crystal Display (LCD) type, plasma type, Organic Light Emitting Diode (OLED) type, a printer, or other types as would occur to those skilled in the art. Moreover, user input 438 may include one or more of a keyboard, mouse, track ball, light pen, and/or microtelecommunicator, to name just a few representative examples.

Figure 10:
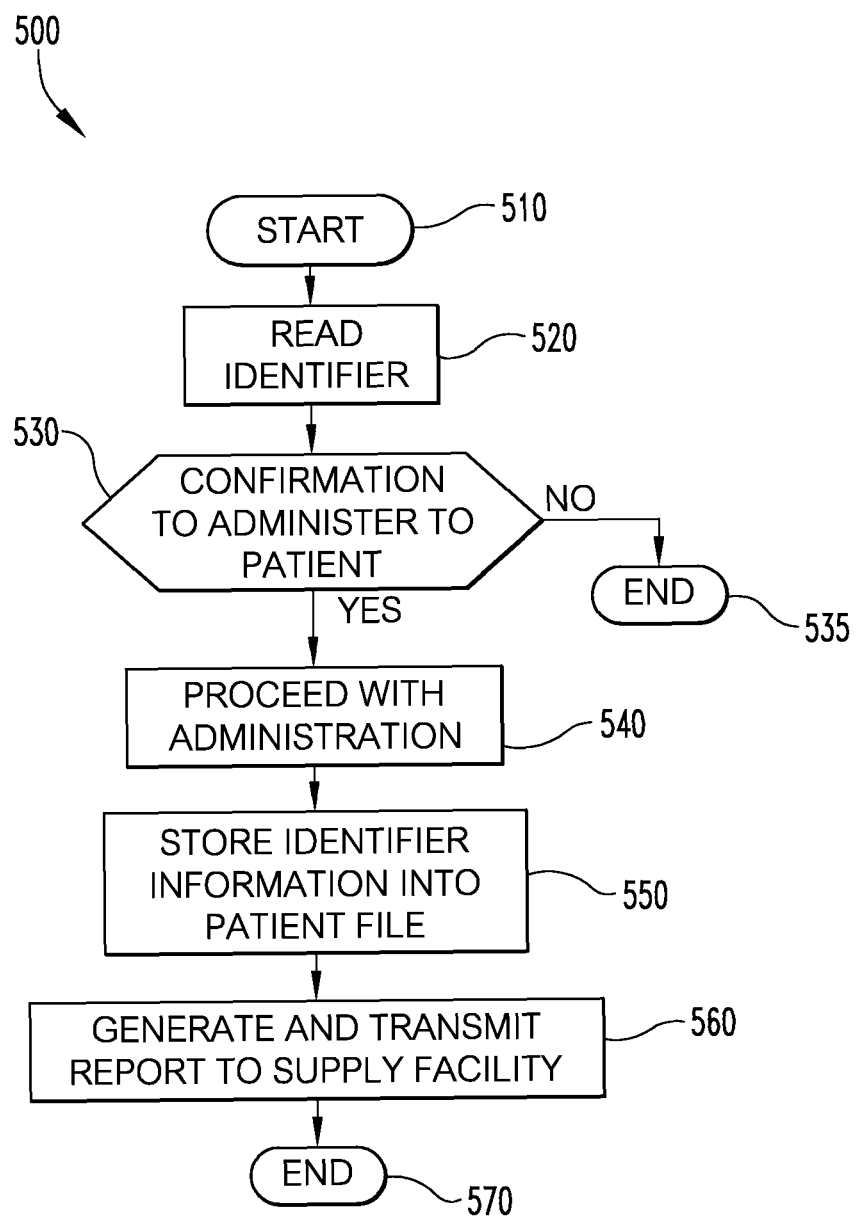
FIG. 10 is a flowchart depicting one procedure for administering the pharmaceutical to the patient at an administration station.

When a healthcare worker is ready to administer the pharmaceutical to a patient at administration station 428, one procedure 500 for doing such is set forth in FIG. 10. For example, at step 510 the healthcare worker can start procedure 500 by preparing delivery device 72 for administration of the pharmaceutical, which includes transferring all or part of the pharmaceutical and identification tag 24 from assembly 10 to delivery device 72 as described above. Identifier 28 can then be read with RF reader/writer 434 at step 520. At step 530, the healthcare worker must determine if there is a confirmation for administering the pharmaceutical to the patient, or if the pharmaceutical is otherwise intended to be administered to the patient. More particularly, the information stored on identifier 28 is compared with the patient's medical history and other information stored in patient file 404 by management computer 402 to determine if the pharmaceutical should be administered to the patient. For example, management computer 402 is configured to detect conflicts between the pharmaceutical and an allergy of the patient or a pharmaceutical currently used by the patient. As another example, management computer 402 is configured to detect a conflict between the pharmaceutical and the patient's treatment plan or the prescription(s) entered into patient file 404 by a physician or other healthcare worker. As yet another example, management computer 402 is operable to determine if the time/date when identifier 28 is read by RF reader/writer 348 corresponds with the time/date identified in patient file 404 for administering the pharmaceutical. In still another example, when identifier 28 identifies a targeted class of recipients for the pharmaceutical, management computer 402 may be operable to determine if the patient is a member of the class. As yet another example, management computer 402 is operable to determine if a conflict exists between the dosing information provided on identifier 28 and the physician's order prescribing administration of the pharmaceutical to the patient. Still, it is contemplated that management computer 402 is operable to detect and consider other aspects of the information stored on identifier and the information stored in patient file 403 which could have a bearing on administration of the pharmaceutical to the patient.

In response to comparing the information stored on identifier 28 and the patient's medical history and other information stored in patient file 404, management computer 402 provides a signal to output 440 which generates an indication to the healthcare worker whether administration of the pharmaceutical to the patient is proper. If administration is proper, output 440 will provide confirmation of same to the healthcare worker and the healthcare worker may continue with administration of the pharmaceutical to the patient, as indicated at step 540 of procedure 500. However, if output 440 does not provide a confirmation to administer the pharmaceutical to the patient, procedure 500 should be ended as indicated at step 535. In addition to the foregoing, output 440 may be responsive to a signal from management computer 402 or information stored on identifier 28 to indicate that the pharmaceutical should not be administered to the patient because it has expired or been recalled. Moreover, when the pharmaceutical is provided in a dosage intended to be administered to a patient belonging to a specific class or classes of patients and identifier 28 identifies the members of the class or classes, it is contemplated that such information may also be used by the healthcare worker to at least preliminarily determine if the pharmaceutical should be administered to the patient in addition to reliance on the indication provided by output 440. For example, this information from identifier 28 can be displayed on output 440 for inspection by the healthcare worker so the healthcare worker can determine if the patient is one of the identified members of the class or classes. For example, where the identified members are males, the healthcare worker will be able to readily ascertain whether the patient is a male or female. If the patient is a member of the class, then the healthcare worker should continue with the indication provided by output 440. However, if the patient is not a member of the class, then the healthcare worker should not administer the pharmaceutical to the patient. This type of secondary consideration based on the information of identifier 28 at least partially safeguards against the situation where the physician's order prescribing administration of the pharmaceutical stored in patient file 404 is incorrect.

Upon administration of the pharmaceutical to the patient, the healthcare worker can enter details of same at user input 438. Alternatively, identifier 28 can automatically provide an indication to RF reader/writer 434 that the pharmaceutical has been administered. It should be appreciated that these details can indicate the time, date, dosage and/or location in administration facility 401 of administration of the pharmaceutical to the patient, just to name a few possibilities. The information regarding administration of the pharmaceutical to the patient is used to update virtual inventory 406 so that additional shipments of the pharmaceutical from supply facility 301 can be requested. In one form, management computer 402 automatically generates and sends an order to supply facility 301 or another distributor or supplier each time the pharmaceutical is administered to the patient. Alternatively, management computer 402 may wait until a threshold number of administrations of the pharmaceutical have occurred and then send a more cumulative order to supply facility 301 or other distributor or supplier.

The information regarding administration of the pharmaceutical to the patient is also stored in patient file 404 to create a history of administration of the pharmaceutical to the patient and indicate that the physician's order corresponding to administration of the pharmaceutical to the patient was followed. The healthcare worker may also utilize user input 438 to enter details into patient file 404 regarding the physical condition of the patient at the time of administration and/or at other times during the patient's visit or admittance to administration facility 401. Examples of details regarding the physical condition of the patient may include the patient's blood pressure, heart rate, temperature, hydration level and/or physical appearance, just to name a few possibilities. As another possibility, the healthcare worker could utilize user input 438 to enter an order prescribing pharmaceutical treatment of the patient into patient file 404. Still, information indicating any side effects of the pharmaceutical experienced by the patient may also be entered into patient file 404 from input 438.

As indicated at step 550 of procedure 500, the information stored in identifier 28 is also stored in patient file 404 in response to administration of the pharmaceutical to the patient. Thus, patient file 404 includes a comprehensive record of the patient's medical history along with the information from identifier 28 providing details of the pharmaceutical. It should be appreciated that patient file 404 may be updated to include the above described information each time a pharmaceutical is administered to the patient by administration facility 401. As indicated by step 560 of procedure 500, a report is generated and transmitted to supply facility 301 regarding the administration of the pharmaceutical to the patient. In one form, management computer 402 automatically generates and sends the report to supply facility 301 each time the pharmaceutical is administered to the patient. Alternatively, management computer 402 may wait until a threshold number of reports have been generated before it sends them to supply facility 301. Indeed, in one form, management computer 402 may be operable to create a comprehensive report of all the pharmaceutical products administered in administration facility 401 and supplied by supply facility 301.

Generally, the report includes non-confidential information stored in patient file 404, all or part of the information stored on identifier 28 and/or the details associated with administration of the pharmaceutical to the patient. It is also contemplated that the report can identify the geographic location and type of administration facility 401. Supply facility 301 may then use the information from the report to determine various aspects of the distribution and administration of the pharmaceutical. For example, supply facility 301 could determine the market penetration of the pharmaceutical, the time between production and administration of the pharmaceutical, the prescribed uses of the pharmaceutical and/or the success of the pharmaceutical in treating certain medical conditions.

When the pharmaceutical has been administered from assembly 10, administration facility 401 may remove flange identification tag 24, return it to supply facility 301, and dispose of container 12 and delivery device 72 in accordance with accepted protocol. Supply facility 301 may then erase or delete the information from identifier 28 and reuse identification tag 24 with another product. Alternatively, assembly 10 including identification tag 24 may be properly disposed of without returning any components to supply facility 301.

As indicated above, system 300 allows supply facility 301 to determine the location/status of assembly 10 at every stage between production and administration of the pharmaceutical to the patient at administration facility 401. Additionally, system 300 allows the information on identifier 28 to be updated or supplemented upon interaction with an RF reader/writer up until administration of the pharmaceutical to the patient. For example, identifier 28 could be updated to include recall information, new dosing guidelines and/or newly discovered contraindications or adverse drug/drug interactions, just to name a few possibilities. While not previously described, it is contemplated that each of RF readers/writers 306, 314, 322, 330, 338, 416, 424 of system 300 can include a user input and an output similar to user input 438 and output 440 described above in connection with administration terminal 432. In this form, the output could provide an indication to a party at each respective RF reader/writer 306, 314, 322, 330, 338, 416, 424 to take a particular action with respect to assembly 10. For example, if the pharmaceutical has expired or been recalled, the indication might instruct the party to remove assembly 10 from distribution and return it to supply facility 301. As a corollary, assembly 10 could be removed from distribution and disposed of or returned to supply facility 301 before it ever reaches administration facility 401. Likewise, the risk of administering a recalled or expired product to the patient is greatly reduced. In addition, the ability to locate and track assembly 10 at every stage of distribution and administration allows supply facility 301 to contact the party in possession of assembly 10 to notify it that assembly 10 has been recalled. As a corollary, the need for the party in possession of assembly 10 to specifically review its inventory to determine if it has products subject to the recall is eliminated.

While assemblies 10, 110, 210 have been described in connection with the administration of a pharmaceutical, it should be understood that the use assemblies 10, 110, 210 in this manner is not limiting. Rather, it should be understood that assemblies 10, 110, 210 can be used in connection with any product having a need to be readily identified while stored in containers 12, 112, 212 and after its transfer from containers 12, 112, 212 to a delivery or other intermediate device. Indeed, in one form, a system which facilitates transfer of the contents of a storage container and an identification tag coupled to the storage container to a delivery or other intermediate device in a single step is provided.

In one embodiment, a system includes a delivery device, a container, a tag configured to store information related to contents of the container and a frangible member coupled to and extending between the tag and the container. The delivery device is engageable with the tag and the tag is removable from the container in engagement with the delivery device upon breakage of the frangible member.

In another embodiment, as assembly includes a container including an internal chamber and a dispensing end, and a tag releasably coupled to the container and configured to store information related to contents of the container. The tag also includes a cannula extending toward the dispensing end of the container. Further, a portion of the cannula is positionable into communication with the internal chamber to facilitate withdrawal of contents from the container.

In yet another embodiment, a system includes a syringe, a vial including a quantity of a pharmaceutical, and a tag releasably coupled to the vial and storing information related to the pharmaceutical. In addition, the syringe is releasably engageable with the tag and the tag is structured to facilitate transfer of at least a portion of the pharmaceutical therethrough from the vial to the syringe when the syringe is engaged with the tag.

In still another embodiment, a method includes providing a vial including a pharmaceutical and a tag storing information related to the pharmaceutical; engaging the tag with a syringe and transferring at least a portion of the pharmaceutical from the vial to the syringe; and removing the tag from the vial while maintaining engagement of the tag with the syringe.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A system, comprising:
   a delivery device;
   a container;
   a tag configured to store information related to contents of said container;
   a frangible member coupled to and extending between said tag and said container, said frangible member normally biasing said tag away from said container and being resiliently compressible to facilitate displacement of said tag toward said container; and
   wherein said delivery device is engageable with said tag and said tag is removable from said container in engagement with said delivery device upon breakage of said frangible member resulting from rotation of said delivery device and tag relative to said container.

2. The system of claim 1, wherein said tag includes a tubular member having a body extending between a proximal end and a distal end spaced from said proximal end toward said container and an internal passage extending between and opening through said proximal and distal ends.

3. The system of claim 2, wherein said proximal end of said tubular member includes an externally threaded portion and said delivery device includes an internally threaded portion structured to engage with said externally threaded portion.

4. The system of claim 2, wherein said tag includes a proximal surface, an oppositely positioned distal surface facing said container, and a recessed portion formed in said proximal surface, and said proximal end of said tubular member is positioned in said recessed portion.

5. The system of claim 4, wherein said recessed portion includes a plurality of teeth extending toward said proximal end of said tubular member and structured to engage with an external surface of said delivery device when said delivery device is engaged with said tag.

6. The system of claim 2, wherein said container includes an internal chamber and said distal end of said tubular member is positionable into communication with said internal chamber to facilitate transfer of contents of said container to said delivery device when said delivery device is engaged with said tag.

7. The system of claim 2, wherein said distal end of said tubular member is positioned into communication with an internal chamber of said container upon displacement of said tag toward said container to facilitate transfer of contents of said container to said delivery device when said delivery device is engaged with said tag.

8. The system of claim 2, wherein said distal end of said tubular member includes a pointed configuration and is releasably coupled with said body.

9. The system of claim 8, wherein a first one of said distal end and said body includes external threading and a second one of said distal end and said body includes internal threading structured to engage with said external threading.

10. The system of claim 1, wherein said frangible member includes a plurality of struts coupled with said container at a first end and with said tag at a second end.

11. The system of claim 10, wherein said tag is releasable from said struts upon rotation of said tag relative to said container.

12. The system of claim 1, wherein said tag includes a machine readable and re-writable identifier configured to store said information related to contents of said container.

13. An assembly, comprising:
a container including an internal chamber and a dispensing end;
a tag releasably coupled to said container by a frangible member and configured to store information related to contents of said container, said tag including a cannula extending toward said dispensing end of said container; and
wherein a portion of said cannula is positionable into said internal chamber to facilitate withdrawal of contents from said container through said cannula.

14. The assembly of claim 13, wherein said frangible member spaces said tag from said container.

15. The assembly of claim 13, wherein said frangible member is resiliently compressible to facilitate displacement of said tag toward said container and positioning of said portion of said cannula into communication with said internal chamber.

16. The assembly of claim 13, wherein said tag is releasable from said frangible member upon rotation of said tag relative to said container.

17. The assembly of claim 13, wherein said cannula includes an elongated body extending between a proximal end structured for engagement with a delivery device and a pointed distal end.

18. The assembly of claim 17, wherein said pointed distal end is releasably coupled to said elongated body.

19. The assembly of claim 17, wherein said tag includes a proximal surface having a recessed portion, and said proximal end of said cannula is positioned in said recessed portion.

20. The assembly of claim 19, wherein said recessed portion includes a plurality of teeth extending toward said proximal end of said cannula.

21. The assembly of claim 13, wherein said tag includes a machine readable and re-writable identifier configured to store said information related to contents of said container.

22. The assembly of claim 13, wherein said container includes an externally threaded portion adjacent to said dispensing end and said tag includes an internally threaded collar structured to engage with said externally threaded portion of said container.

23. The assembly of claim 13, wherein said container includes an externally threaded portion adjacent to said dispensing end and said tag includes a pair of opposing pins each having an end biased into engagement with said externally threaded portion of said container.

24. A system, comprising:
a syringe;
a vial including an internal chamber holding a quantity of a pharmaceutical and a membrane sealing said internal chamber;
a tag releasably coupled to said vial by a frangible member and storing information related to said pharmaceutical, said tag including a cannula extending between a proximal end structured for engagement with said syringe and a distal end structured for penetrating said membrane to position a portion of said cannula into said internal chamber; and
wherein said syringe is releasably engageable with said tag and said tag is structured to facilitate transfer of at least a portion of said pharmaceutical therethrough from said vial to said syringe when said syringe is engaged with said tag.

25. The system of claim 24, wherein said tag is removable from said vial in engagement with said syringe upon breakage of said frangible member by rotation of said tag relative to said container.

26. The system of claim 24, wherein said tag includes a machine readable and re-writable identifier storing said information related to said pharmaceutical.

27. The system of claim 24, wherein said quantity of said pharmaceutical corresponds to a single dosage.

28. The system of claim 24, wherein said vial includes an externally threaded portion and said tag includes an internally threaded collar structured to engage with said externally threaded portion of said vial.

29. The system of claim 24, wherein said vial includes an externally threaded portion and said tag includes a pair of opposing pins each having an end biased into engagement with said externally threaded portion of said vial.

30. A method, comprising:
providing a vial including a pharmaceutical and a tag storing information related to the pharmaceutical, said tag including a cannula;
engaging the tag with a syringe and axially displacing the tag toward the vial to position a portion of the cannula into the vial;
withdrawing at least a portion of the pharmaceutical from the vial through the cannula to the syringe; and
removing the tag from the vial while maintaining engagement of the tag with the syringe.

31. The method of claim 30, wherein the tag is coupled to the vial by a frangible member, and removing the tag includes rotating the syringe and tag relative to the vial to sever the tag from the frangible member.

32. The method of claim 30, wherein the tag includes a machine readable and re-writable identifier storing the information related to the pharmaceutical.

* * * * *